United States Patent
Mucha

(10) Patent No.: US 11,730,549 B2
(45) Date of Patent: *Aug. 22, 2023

(54) METHOD AND DEVICE FOR NAVIGATING ACTIVE SURGICAL INSTRUMENTS

(71) Applicant: INTERSECT ENT GMBH, Hennigsdorf (DE)

(72) Inventor: Dirk Mucha, Berlin (DE)

(73) Assignee: FIAGON GMBH

( * ) Notice: Subject to any disclaimer, the term of this patent is extended or adjusted under 35 U.S.C. 154(b) by 0 days.

This patent is subject to a terminal disclaimer.

(21) Appl. No.: 17/374,865

(22) Filed: Jul. 13, 2021

(65) Prior Publication Data

US 2022/0104882 A1 Apr. 7, 2022

Related U.S. Application Data

(63) Continuation of application No. 14/915,318, filed as application No. PCT/EP2014/068447 on Aug. 29, 2014, now Pat. No. 11,109,915.

(30) Foreign Application Priority Data

Aug. 30, 2013 (DE) .......................... 102013217328.8

(51) Int. Cl.
*A61B 34/20* (2016.01)
*A61B 5/06* (2006.01)
*A61B 90/00* (2016.01)
*A61B 17/00* (2006.01)

(52) U.S. Cl.
CPC .............. *A61B 34/20* (2016.02); *A61B 5/062* (2013.01); *A61B 90/00* (2016.02); *A61B 17/00* (2013.01); *A61B 2034/2051* (2016.02); *A61B 2034/2072* (2016.02); *A61B 2090/08021* (2016.02)

(58) Field of Classification Search
CPC ......... A61B 34/20; A61B 5/062; A61B 90/00; A61B 17/00; A61B 2034/2051; A61B 2034/2072; A61B 2090/08021
See application file for complete search history.

(56) References Cited

U.S. PATENT DOCUMENTS

| | | | | |
|---|---|---|---|---|
| 6,369,564 | B1 * | 4/2002 | Khalfin | G01B 3/1084 324/207.17 |
| 11,109,915 | B2 * | 9/2021 | Mucha | A61B 5/062 |
| 2004/0082849 | A1 * | 4/2004 | Schweikard | G06T 19/003 600/425 |

(Continued)

*Primary Examiner* — Sean D Mattson

(57) ABSTRACT

A method for detecting a position and an operating state of an active surgical instrument. The active surgical instrument emits or influences/modifies at least one electromagnetic field in an active operating state. The method includes the steps of positioning a first sensor in order to detect the electromagnetic field emitted or influenced by the active surgical instrument is the active operating state at a known position, detecting the electromagnetic field emitted or influenced by the active surgical instrument in the active operating state by means of the first sensor, generating an output signal by means of the first sensor, the output signal indicating the detection of the electromagnetic field emitted or influenced by the active surgical instrument by means of the first sensor, and ascertaining the position and operating state of the active surgical instrument on the basis of the output signal and the known position of the first sensor.

17 Claims, 2 Drawing Sheets

(56) References Cited

U.S. PATENT DOCUMENTS

| | | | | |
|---|---|---|---|---|
| 2004/0199072 A1* | 10/2004 | Sprouse | ............... | A61B 5/062 |
| | | | | 5/601 |
| 2006/0058604 A1* | 3/2006 | Avinash | ............... | A61B 5/066 |
| | | | | 600/407 |
| 2006/0211914 A1* | 9/2006 | Hassler, Jr. | ........... | A61F 5/0053 |
| | | | | 600/587 |
| 2008/0275334 A1* | 11/2008 | Berting | ............... | A61B 34/20 |
| | | | | 600/424 |
| 2009/0069671 A1* | 3/2009 | Anderson | ............ | A61B 5/062 |
| | | | | 600/424 |
| 2012/0007747 A1* | 1/2012 | Boike | ............... | E21B 47/024 |
| | | | | 340/856.3 |
| 2013/0060278 A1* | 3/2013 | Bozung | ............... | A61B 17/16 |
| | | | | 606/205 |
| 2014/0148808 A1* | 5/2014 | Inkpen | ............... | A61B 90/06 |
| | | | | 73/866.5 |

* cited by examiner position a first sensor for detecting a least one electromagnetic field emanating from, or influenced by, an active surgical instrument in an active operating state thereof at a known location detect by the first sensor the electromagnetic field emanating from, or influenced by, the active surgical instrument in the active operating state thereof generate an output signal by the first sensor, the output signal indicating the detection by the first sensor of the electromagnetic field emanating from, or influenced by, the active surgical instrument establish a location and operating state of the active surgical instrument on the basis of the output signal and the known location of the first sensor, and generating location data detect a position data of the active surgical instrument by a position detection unit of an instrument sensor arranged at the active surgical instrument

FIG. 2

METHOD AND DEVICE FOR NAVIGATING ACTIVE SURGICAL INSTRUMENTS

CROSS-REFERENCE TO RELATED APPLICATIONS

This application is a continuation of U.S. patent application Ser. No. 14/915,318 filed on Feb. 29, 2016, which is the U.S. National Stage of International Application Number PCT/EP2014/068447 filed on Aug. 29, 2014, which application claims priority under USC § 119 to German Patent Application No. 102013217328.8 filed on Aug. 30, 2013. All applications are hereby incorporated by reference in their entirety.

TECHNICAL FIELD

The invention relates to a method for detecting a location and operating state of an active surgical instrument in a work region by means of a sensor, the active surgical instrument emitting at least one electromagnetic field in a switched-on operating state and the electromagnetic field being detected by the sensor. Furthermore, the invention relates to a medical system for localizing active surgical instruments in a work region, with at least one active surgical instrument that is embodied to emit an electromagnetic field in the active operating state.

BACKGROUND

In invasive surgical interventions, surgical instruments are moved in an operating region in the interior of a patient by a surgeon during an operation. An operating region refers to the space in the interior of the patient which, potentially or effectively, is affected by the employed surgical instruments during the operation. The operation includes the insertion and removal of surgical instruments into the body of the patient and out of the body of the patient, as well as the movement of the surgical instruments within the body of the patient and the use of the surgical instruments in an intervention region which is arranged in the operating region and precisely predefined. The intervention region refers to the part in the operating region which is to be worked on by the surgeon. By way of example, this can relate to the tissue to be removed or vessels to be closed. Accordingly, an operating region may comprise a plurality of intervention regions. A multiplicity of sensitive structures lie next to the intervention regions in the operating region and they are to be preserved from damage by the surgical instruments. The sensitive structures include, for example, vessels, organs, nerves, muscles, ligaments, sinews and other, generally intact tissue which is intended to be maintained in order to restrict the effects of the operation to a necessary minimum, as any further impairment of the body of the patient during the operation may increase the health risk to the patient and have a negative influence on the result of the operation.

Therefore, position detection systems are regularly used when performing invasive surgical interventions. Position detection systems assist the surgeon when establishing the position—i.e. the location and alignment—of surgical instruments in the operating region. Known position detection systems serve, in particular, to improve the navigation of the surgical instrument into an intervention region in the body of the patient, the navigation of the surgical instrument while carrying out an operative measure and the navigation of the surgical instrument out of the body of the patient. As a result of this, it is possible to improve the result and the efficiency of the operation to be carried out. Moreover, precise navigation of the surgical instrument can reduce the risk of inadvertent impairment of, or damage to, surrounding tissue or neural pathways, potentially at risk, in the operating region.

Conventionally, position detection systems detect the location and alignment of at least one medical instrument, e.g. a surgical instrument, during the operation and transform the detected location coordinates such that a location and alignment of the instrument can be superposed into e.g. images of the patient and, in particular, optional spatial depictions of the intervention region. It is possible to establish position information of a multiplicity of different surgical instruments in many position detection systems. The detected position information is usually visualized on a monitor together with planning data obtained presurgery and/or image data obtained during the surgery. To this end, sensors (which are also referred to as localizers) are arranged at determinable points of the patient and of the surgical instruments, the output signals of which sensors are determinable as position information in the operating region by an evaluation unit of the position detection system.

By way of example, it is known to provide different medical instruments, such as e.g. pointer instruments, suction devices, forceps, needles, scalpels, electrotomes, cauteries, and the like with localizers (instrument sensors) for establishing position information for such a position detection system and to register the respective medical instrument in the position detection system. During the registration, the position of a reference point—usually the work point of the instrument tip—is calibrated by means of a localizer (location sensor) at the instrument relative to a known point at the patient (or an object) and transmitted to the position detection system. In this manner, the alignment of the medical instrument and the position of the reference point determined by the position detection system can be related to known points at the patient or an object in order subsequently to be able to transform the coordinates of the reference point of the instrument detected by the position detection system into a coordinate system underlying the image data of the patient. On the basis of this data, it is possible to depict on the monitor an image, true to position, of the medical instrument together with the available pre-surgical and/or intraoperative image data.

Such position detection systems may comprise localizers which, for example, operate optically, with ultrasound or in an electromagnetic manner. By way of example, position detection systems operating on the basis of electromagnetic induction are known; these have a field generator, which is arranged next to the patient and generates a generally alternating electromagnetic field in the work region. A localizer which has a plurality of sensor coils with a known relative position in relation to one another is arranged at a surgical instrument to be navigated in the work region. The alternating electromagnetic field induces electric currents in these sensor coils in a manner dependent on the alignment of the respective sensor coil in relation to the alternating electromagnetic field, which currents are characteristic for the alignment and location of the respective coil in the alternating electromagnetic field. An evaluation unit measures the induced currents and, taking into account the known position of the coils in relation to one another, therefore establishes the position of the sensor coils in the alternating electromagnetic field. During the registration or calibration process, the instrument tip of the surgical instrument should initially be guided with a predetermined alignment to a reference point defined in the position detection system and the position of the localizer should be determined when the reference point is reached. Hence, the position in the work region of a surgical instrument equipped with the sensor coils is determinable by the position detection system.

The aforementioned position detection systems are disadvantageous in that they are substantially only suitable for detecting the position of passive surgical instruments such as e.g. scalpels or scissors. Active surgical instruments, such as e.g. drills, cauteries or oscillating saws, emit an electromagnetic field, which is superimposed on the alternating electromagnetic field from the field generator, and the interferences resulting therefrom can have a direct effect on the current induced in the sensor coil. This leads to falsification of the position data of the sensor coil, and hence of the surgical instrument, established by the evaluation unit. Moreover, active surgical instruments in an active operating state harbor an increased risk of damage to adjacent tissue by way of the active instrument part.

WO 02/076302 has disclosed a method and a device system for tissue ablation and for tissue treatment, wherein the position of an active surgical instrument in the operating region is detected by way of an optical position determination apparatus and the tissue ablation and the tissue ablation rate in the intervention region are determined on the basis of the therefore determinable change in position of the active surgical instrument. The operation progress is establishable on the basis of these data and the operating state of the active surgical instrument is controllable. Here, the power of the active surgical instrument can be throttled in the case of the imminent achievement of the operation target, i.e. the performed ablation of a predetermined tissue volume, and the active surgical instrument can be switched off when the operation target is reached.

A disadvantage of this method and device system is that use is only made of optical position detection means which, on account of a restricted field of view and strong dirtying of the sensors, e.g. by blood, in the operating region, are not suitable for many surgical interventions. Moreover, the closed-loop control of the operating state of the active surgical instrument merely takes into account the operation progress; sensitive structures which can potentially be damaged by the surgeon are not taken into account.

Therefore, the present invention is based on the object of providing a method and a medical system for detecting a location and operating state of active surgical instruments in a work region, which enable a more precise establishment of the location of the active instrument in the work region than what is known from the prior art and which reduce the risk of inadvertent damage by the active surgical instrument to objects arranged in the work region, in particular in an active operating state of the active surgical instrument.

SUMMARY

According to the invention, this object is achieved by a method for detecting a location and operating state of an active surgical instrument, the active surgical instrument emitting at least one electromagnetic field or influencing and therefore modifying a given electromagnetic field in a switched-on operating state. The method comprises the following method steps: positioning at least one first sensor for detecting at a known location the electromagnetic field emanating from the active surgical instrument in the active operating state thereof, detecting by means of the at least one first sensor the electromagnetic field emanating from, or changed by, the active surgical instrument in the active operating state thereof, generating an output signal by the at least one first sensor, the output signal indicating the detection by the at least one first sensor of the electromagnetic field emanating from, or changed by, the active surgical instrument; and establishing a location and operating state of the active surgical instrument on the basis of the output signal or the output signals and the known location or locations of the at least one first sensor.

Instead of explicitly establishing a location and operating state of the active surgical instrument, it is also possible to directly use the output signal of the at least one first sensor indicating the strength of, or change in, the electromagnetic field in order, for example, to control the operating state of the active surgical instrument since the output signal always contains information about a relative vicinity between an instrument and a first sensor and therefore also always implicitly contains location data.

Thus, provision can be made for one or more first sensors. Therefore, the first sensor can either directly detect an electromagnetic field emanating from the active surgical instrument or detect a change in a surrounding electromagnetic field caused by the active operating state of the active surgical instrument; if necessary, both options are also possible. It is expedient to determine the dependence of the electromagnetic field emitted or changed by the active surgical instrument on the operating state of the active surgical instrument by way of a reference measurement. To this end, field parameters such as e.g. strength and frequency of the electromagnetic field are taken into account as a function of the operating state. A family of characteristics of the active surgical instrument is generable from the measurement data of the reference measurement. This family of characteristics should be accordingly taken into account when determining the location and the operating state of the active surgical instrument.

Preferably, the output signal generated by the respective first sensor has a signal vale or level which indicates a strength detected by the respective first sensor or the degree of the change in the electromagnetic field of the active surgical instrument. As a result of this, it is possible to draw conclusions from the signal value or level of the output signal about the strength of, or the change in, the detected electromagnetic field at the sensor. Hence, a quantitative reflection of the strength of, or the change in, the detected electromagnetic signal is possible. If a location of the first sensor, a characteristic of the electromagnetic field and a ratio between detected strength of, or change in, the electromagnetic field and the strength of the output signal of the first sensor are known, the location of the surgical instrument in the work region is accordingly established on the basis of the signal value or level of the output signal of the first sensor. More precise location data can be generated with a plurality of first sensors, for example in the style of a triangulation.

The level of the output signal generated by the respective first sensor reflecting the detected strength of, or change in, the electromagnetic field of the active surgical instrument can be used in different advantageous ways, for example for automatically influencing the active surgical instrument, or else for generating a signal perceivable by a medical practitioner and indicating to the medical practitioner the approach of the active surgical instrument to a target region. Such a perceivable signal may be e.g. optical or acoustic, for example a sound, the frequency and/or modulation of which changes with an (optionally too close) approach to a target structure or by optical highlighting of critical structures in a computed tomography image obtained presurgery or intraoperatively. Particularly preferably, different operating states of the active surgical instrument are detected and taken into account when establishing the location of the active surgical instrument.

Apart from the detected strength of, or change in, the electromagnetic field, the automatic influencing of the active medical instrument or the generated perceivable signal can also depend on the activity state of the active medical instrument. In the case of an acoustic signal, the frequency can e.g. indicate the detected strength of the electromagnetic field, while a modulation (e.g. uninterrupted sound vs. interrupted sound) can simultaneously indicate the activity state of the active medical instrument.

In particular, it is possible to generate a warning signal when, depending on the activity state of the active medical instrument, there is an approach to a target structure that is too close.

It is preferable for the operating state of the active surgical instrument to be controlled in a manner dependent on the generated output signal.

More preferably, the active surgical instrument is throttled if the first sensor detects a strength of, or a change in, the electromagnetic field that exceeds a selected first threshold. By way of example, the throttling can be carried out as a function of the detected strength of the electromagnetic field. What is ensured hence is that the operating state of the active surgical instrument is controllable in a manner dependent on the location of the active surgical instrument in the work region. Moreover, an unnecessary power uptake of the active surgical instrument can be reduced and inadvertent damage of objects in the work region by the active surgical instrument can be prevented.

If the output signal of the first sensor reflecting the strength of, or change in, the electromagnetic field for example indicates an approach to possibly sensitive target structures, the active surgical instrument can also be controlled in such a way that there is haptically perceivable feedback, e.g. an intermittent operation of the active surgical instrument which can be perceived by a medical practitioner because the device "jerks".

Particularly preferably, the active surgical instrument is switched off if the first sensor detects a strength of, or a change in, the electromagnetic field that is greater than a selected second threshold. The second threshold is greater than the first threshold. What can be prevented by this measure is the active surgical instrument having an active operating state in the case of an unwanted collision with an object in the work region and the object being damaged thereby.

Preferably, a refresh rate of a display unit is set in a manner dependent on the established operating state of the active surgical instrument. In this manner, e.g. the characteristic of the cutting edges of the active surgical instrument is displayable in an improved manner for an operating person.

Particularly preferably, a rotational speed of a work tip of the active surgical instrument corresponds to an integer multiple of the set refresh rate. When the rotational speed of the work tip of the active surgical instrument is changed, the refresh rate of the display is adapted accordingly in order always to correspond to an integer multiple of the rotational speed of the work tip of the active surgical instrument.

More preferably, the position data of the active surgical instrument is detected by a position detection unit by means of an instrument sensor (i.e. a localizer at the instrument) arranged at the active surgical instrument. The position comprises both the location in space and the alignment. To this end, the instrument sensor can comprise e.g. sensor coils and the position determination unit can comprise a field generator which generates an alternating electromagnetic field in the work region. This is advantageous in that the position of the active surgical instrument in the work region is also determinable when the active surgical instrument is in an inactive operating state.

Preferably, there is a comparison of the location data, detected by means of the first sensor, and the position data, detected by means of the instrument sensor, of the active surgical instrument and/or a location correction value is formed from associated location-position data pairs. Therefore, it is possible e.g. to correct interferences of the electromagnetic field of the active surgical instrument in an alternating electromagnetic field of the position determination unit, which can lead to errors when determining the position. As a result of this measure, the accuracy of determining the position of the active surgical instrument can be improved.

Since an electromagnetic field emanating from an active medical device can impair an exact detection of the location of the instrument by means of an instrument sensor, provision can be made of a plurality of first sensors for a more exact detection of the position, said first sensors enabling a detection of the position e.g. by way of triangulation.

Alternatively or additionally, the active medical instrument can also be equipped with one or more ultrasonic sensors. With the aid of an ultrasonic sensor, it is possible, in a manner known per se, to detect changes in density in the tissue in an image-like manner. The advantage of this is that such images obtained by means of ultrasound are not disturbed by electromagnetic fields.

Preferably, the operating state of the active surgical instrument is transmitted from the active surgical instrument and/or a control unit of the active surgical instrument to the location detection unit and/or position detection unit. Due to the thus obtained parameter of the operating state of the active surgical instrument, the location detection unit and/or position detection unit can monitor the family of characteristics of the active surgical instrument by means of the output signal generated by the first sensor and carry out a new calibration of the active surgical instrument in the case of a pre-definable deviation.

Moreover, the aforementioned object is achieved by a medical system for localizing active surgical instruments in a work region, with at least one active surgical instrument, the active surgical instrument being embodied to emit an electromagnetic field in the active operating state. The medical system has a location detection unit for establishing the location of the active surgical instrument in the work region and at least one first sensor. The first sensor is arrangeable at a known location in the work region and embodied to detect the electromagnetic field of the active surgical instrument and to transmit an output signal indicating the detected parameters of the electromagnetic field to the location detection unit, the location detection unit being embodied to establish the location of the active surgical instrument on the basis of the output signal and the location of the first sensor.

Preferably, the medical system has a position detection system with a position detection unit, a field generator and an instrument sensor, the instrument sensor being arrangeable or arranged at the active surgical instrument and embodied to detect an alternating electromagnetic field generated by the field generator and to transmit a signal indicating the detected alternating electromagnetic field to the position detection unit. The position detection unit is embodied to establish position data of the active surgical instrument on the basis of the detected signal and the known alternating electromagnetic field generated by the field generator.

Preferably, the location detection unit and/or position detection unit is configured to compare the location data and the position data of the active surgical instrument and to establish a corrected location and/or position of the active surgical instrument therefrom. Therefore, a position of the active surgical instrument determined incorrectly as a result of interference between the electromagnetic field of the active surgical instrument and the alternating electromagnetic field of the field generator can be corrected.

Preferably, the medical system has a display unit for depicting, true to the position, at least one active surgical instrument detected by the position detection unit in the work region and obtained image data of an object arranged in the work region. The image data can comprise both individual images, such as e.g. x-ray images or CT recordings, and video images, with the medical system preferably being embodied to record video images and display these without delay, where possible, or only with little delay.

In an advantageous embodiment of the invention, the medical system has a data interface for transmitting the operating state of the active surgical instrument from the active surgical instrument and/or an instrument control unit of the active surgical instrument to the position detection unit and/or location detection unit. The data interface can be embodied for wired or wireless transmission, e.g. by radio or optically, of the operating state of the active surgical instrument.

Preferably, the active surgical instrument has an electric motor which, depending on the operating state of the active surgical instrument, emits an interference signal. Conventional electric motors have a magnet and coils, and are based on the principle of induction. Therefore, they have an electromagnetic field during operation, which is detectable by sensors.

BRIEF DESCRIPTION OF THE DRAWINGS

The invention is intended to be explained in more detail below on the basis of an exemplary embodiment, with reference being made to the drawing. In detail:

FIG. 2 shows a flow chart corresponding to the steps of the medical system according to the invention for localizing and determining the operating state of active surgical instruments.

DETAILED DESCRIPTION

Figure 1:
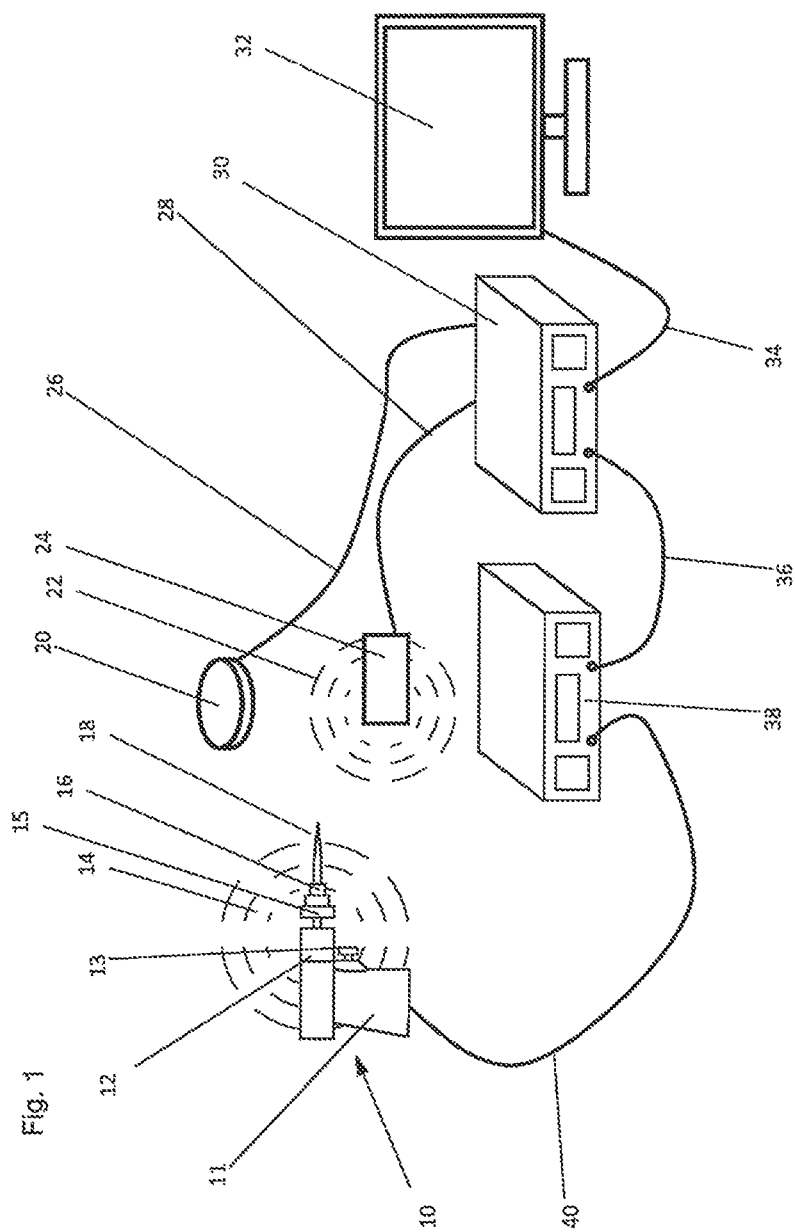
FIG. 1 shows a schematic view, not necessarily to scale, of a medical system according to the invention for localizing and for determining the operating state of active surgical instruments.

A medical system according to the invention which is embodied to determine the location of an active surgical instrument comprises at least one location detection unit and a first sensor 20. A medical system for determining the position of an active surgical instrument 10 in a work region is e.g. expandable using this medical system. Such a medical system for determining the position of an active surgical instrument comprises a position detection unit, a field generator 24 for emitting an alternating electromagnetic field 22 in a work region, an instrument sensor 16 and a display unit 32 for displaying, true to scale, the active surgical instrument 10. In the active operating state, the active surgical instrument 10 emits an electromagnetic field 14.

The medical system in accordance with the exemplary embodiment depicted in FIG. 1 comprises an active surgical instrument 10, which is embodied as a surgical drill. The active surgical instrument 10 has a handle 11 and an actuator 13, arranged at the handle 11, for setting the rotational speed of an instrument tip 18. For the purposes of driving the instrument tip 18, the active surgical instrument 10 has an electric motor 12 which is covered in this illustration, wherein the electric motor 12 is arranged in the vicinity of the instrument tip 18 and it emits the electromagnetic field 14 during operation. The instrument tip 18 is held detachably at the active surgical instrument by way of a clamping apparatus 15. Hence, the instrument tip 18 can easily be disassembled due to e.g. wear and tear or dirtying and it can be replaced by a new instrument tip 18 or returned to a state which satisfies the requirements of the instrument tip 18.

During operation, the electric motor 12 emits an electromagnetic field 14 which is depicted symbolically in the figure by concentric circle segments. The electromagnetic field 14 propagates in a substantially spherical manner from the electric motor 12 and has a field frequency and a field strength. The active surgical instrument 10 is connected to an instrument control unit 38 by means of an instrument cable 40. The instrument control unit 38 supplies power to the active surgical instrument 10 by way of the instrument cable 40.

A first sensor 20 for detecting the electromagnetic field 14 is connected to a navigation unit 30 by way of a sensor line 26. In this embodiment, the navigation unit 30 comprises a location detection unit and a position detection unit. Alternatively, the location detection unit and position detection unit can also be embodied as separate modules such that, for example, a medical system which already has a position detection unit can, without much outlay, be complemented by a location detection unit with a first sensor.

The first sensor 20 is arrangeable in a work region, e.g. in the vicinity of an object (not depicted here), with the object being potentially damageable by the instrument tip 18, particularly in the active operating state of the active surgical instrument. When the active surgical instrument 10 in the active operating state approaches the first sensor 20, the electromagnetic field 14 induces a current in the first sensor 20 which, as an output signal, is transmitted to the navigation unit 30 by way of a sensor line 26. Since the position data of the first sensor 20 in the work region are known, the navigation unit 30 can determine the location of the electric motor 12 and hence also the location of the active surgical instrument 10 in the work region due to the characteristic of the received output signal of the first sensor 20. If no signal is received by the first sensor 20, this means either that the active surgical instrument 10 is too far away from the first sensor 20 or that it is in the passive operating state, i.e. switched off.

For the purposes of visualizing the determined location data of the active surgical instrument 10, the navigation unit 30 is connected to a display unit 32 by way of a monitor cable 34. Hence, it is possible to display e.g. the instrument tip 18 on the display unit. Expediently, these image data are depicted on the display unit 32 in a manner superposed with further image data, such as e.g. CT, x-ray or video image data, of the operating region of the patient, which are obtained either presurgery or intraoperatively.

The navigation unit 30 is connected by way of a generator cable 28 to a field generator 24 which generates an alternating electromagnetic field 22 depicted schematically in the figure by means of concentric circular segments. This alternating electromagnetic field 22 is detectable by an instrument sensor 16 arranged in the vicinity of the instrument tip 18 at the active surgical instrument 10. A current is induced in the instrument sensor 16 by the alternating electromagnetic field 22 in a manner dependent on the position of the instrument. sensor 16, said current being transmitted by way of the instrument cable 40 to the instrument control unit 38. By way of a connection cable 36, this induced current is forwarded to the navigation unit 30 and evaluated there in order to determine the position of the active surgical instrument 10 relative to the patient and display this on the display unit 32. This additional option for determining the position is advantageous in that the position of the active surgical instrument 10 relative to the patient is also determinable if the active surgical instrument 10 is inactive and the electric motor 12 does not generate an electromagnetic field 14. The system can be configured in such a way that the field generator 24 is inactive or only operated in a pulsating manner if the active surgical instrument 10 is active and the electric motor 12 generates an electromagnetic field 14 so as to prevent or compensate possible measurement interference by interference between the electromagnetic field 14 of the electric motor 12 and the alternating electromagnetic field 22 of the field generator 24.

If the location detection unit or navigation unit 30 determines that the active surgical instrument 10 or the instrument tip 18 drops below a first minimum distance from an object (not depicted in this illustration) in the work region, a control signal can be transmitted from the location detection unit or navigation unit 30 to the instrument control unit 38 for the purposes of throttling the power of the active surgical instrument 10. By way of example, this throttling can be carried out with jumps or continuously. The throttling can also be carried out directly at the active surgical instrument 10, without transmitting a control signal to the instrument control unit 38. To this end, an e.g. preferably regulable resistor could be arranged at the electric motor 12.

Alternatively or additionally, a warning, e.g. an acoustic or optical signal, can be output to the user. By way of example, there can be a color change on the display unit 32 as an optical signal. The color change can also extend over a spectrum and it can be carried out in a manner dependent on the distance between the instrument tip 18 of the active surgical instrument 10 and the object in the work region. As a result of this, the user can be warned that a collision with an object in the work region is potentially imminent and that the active surgical instrument 10 should be removed from this object again. By throttling the active surgical instrument 10, damage to the object by the active surgical instrument in the case of a collision is reduced further. Furthermore, the throttling is also a haptic and/or possibly audible and/or visible indication for the user that the active surgical instrument 10 has dropped below a first minimum distance to a specific object in the work region.

If the location detection unit or navigation unit 30 furthermore determines that the active surgical instrument 10 has dropped below a second minimum distance to the object in the work region, with the second minimum distance preferably being smaller than the first minimum distance, a further control signal can be transmitted from the location detection unit or navigation unit 30 to the instrument control unit 38 in order to deactivate the active surgical instrument 10. Alternatively, the active surgical instrument 10 can be switched off directly at the active surgical instrument 10, for example by cutting the power supply at the electric motor 12, and without the transmission of a control signal to the instrument control unit 38. As a result of this, the risk of damaging an object arranged in the work region by an active surgical instrument 10 in the case of a collision with a sensitive structure of the patient is reduced since the active surgical instrument 10 in the deactivated operating state has fewer potential risks than in the active operating state. Moreover, as a result of the standstill of the active surgical instrument 10, the operator is prompted to navigate the active surgical instrument 10 away from the object in the work region.

A flow chart for the above-described methodology is shown in FIG. 2.

This exemplary embodiment is merely intended to schematically illustrate the subject matter of the present invention and not intended to restrict the invention to this specific embodiment. Configurations are provided within the scope of the invention, in which the navigation unit 30 and the instrument control unit 38 form a common unit. Wired connections may optionally also be replaced by wireless connections. The number of sensors employed is expediently greater than the number in the illustrated exemplary embodiment in order to improve the accuracy of the navigation system. By way of example, a first sensor can be a sensor unit and can likewise comprise a group of first sensors. Furthermore, means can be provided which regulate the characteristic of the alternating electromagnetic field 22 of the field generator 24 in a manner dependent on the characteristic of the electromagnetic interference field 14 of the electric motor 12.

LIST OF REFERENCE SIGNS

10 Active surgical instrument
11 Handle
12 Electric motor
13 Actuator
14 Electromagnetic field
15 Clamping apparatus
16 Instrument sensor
18 Instrument tip
20 First sensor
22 Alternating electromagnetic field
24 Field generator
26 Sensor line
28 Generator cable
30 Navigation unit
32 Display unit
34 Monitor cable
36 Connection cable
38 Instrument control unit
40 Instrument cable

The invention claimed is:

1. A method for detecting a location and operating state of a surgical instrument having an active operating state, and an inactive state, comprising:
    positioning a first sensor at a known location, the first sensor configured to detect a first electromagnetic field emitted from the surgical instrument when in the active operating state;
    detecting the first electromagnetic field with the first sensor;
    generating an output signal from the first sensor, the output signal indicating the detection by the first sensor of the first electromagnetic field emitted from the surgical instrument in the active operating state; and establishing the location and the operating state of the surgical instrument in the active operating state on the basis of the output signal and the known location of the first sensor;

generating location data, the location data corresponding to the established location;

controlling the operating state of the surgical instrument based on the output signal;

detecting a second alternating electromagnetic field generated by a field generator with an instrument sensor; and generating an induced current dependent on a position of the instrument sensor, and evaluating the induced current so as to determine a position of the surgical instrument relative to a patient when the surgical instrument is in the inactive state.

2. The method of claim 1, wherein the output signal generated by the first sensor has a signal value that indicates a change in the first electromagnetic field detected by the first sensor.

3. The method of claim 1, wherein the output signal indicates that the surgical instrument is a minimum distance from an object in a work region.

4. The method of claim 3, wherein a warning is provided when a distance between the surgical instrument and the object in the work region has dropped below the minimum distance.

5. The method of claim 1, wherein power to the surgical instrument is throttled if the first sensor detects a strength of the first electromagnetic field that is greater than a selected first threshold.

6. The method of claim 5, wherein the surgical instrument in the active operating state is switched off if the first sensor detects that the strength of the first electromagnetic field is greater than a selected second threshold, the selected second threshold being greater than the selected first threshold.

7. The method of claim 1, wherein there is a comparison of the location data, generated by the first sensor, and position data, wherein the position data corresponds to the position of the surgical instrument detected by the instrument sensor, and wherein a location correction value is formed from associated location-position data pairs.

8. The method of claim 1, wherein a refresh rate of a display unit is set in a manner dependent on the established operating state of the surgical instrument.

9. The method of claim 8, wherein a rotational speed of a work tip of the surgical instrument corresponds to an integer multiple of the set refresh rate.

10. The method of claim 1, further comprising displaying the surgical instrument on a display unit.

11. The method of claim 10, wherein the displayed surgical instrument is superimposed on image data.

12. The method of claim 1, further comprising calibrating the surgical instrument.

13. A medical system for localizing and for determining an operating state of a surgical instrument in a work region of a patient, the surgical instrument having an active operating state and an inactive state, the surgical instrument when in the active operating state configured to emit a first electromagnetic field, comprising:

a first sensor positioned at a known location in the work region, the first sensor configured to detect the first electromagnetic field emitted from the surgical instrument when in the active operating state and configured to generate an output signal indicating the detection by the first sensor of the first electromagnetic field;

a location detection unit, the location detection unit configured to establish a location and the operating state of the surgical instrument in the active operating state on the basis of the output signal generated by the first sensor and the known location of the first sensor, and to generate location data;

a navigation unit configured to determine a position of the surgical instrument relative to a patient, and to generate position data; and an instrument sensor on the surgical instrument configured to detect a second alternating electromagnetic field generated by a field generator, wherein the operating state of the surgical instrument is controlled by the output signal generated by the first sensor.

14. The medical system of claim 13, wherein the location detection unit is configured to compare the location data and the position data of the surgical instrument, and to establish a corrected location or corrected position of the surgical instrument.

15. The medical system of claim 13, wherein the navigation unit is configured to compare the location data and the position data of the surgical instrument, and to establish a corrected location or corrected position of the surgical instrument.

16. The medical system of claim 13, further comprising a display unit for displaying the surgical instrument in the work region of the patient.

17. The medical system of claim 13, further comprising a data interface configured to transmit the operating state of the surgical instrument from the surgical instrument.

* * * * *